(12) United States Patent
Madanat

(10) Patent No.: US 9,101,527 B2
(45) Date of Patent: Aug. 11, 2015

(54) COMBINED CARDIO PULMONARY RESUSCITATION (CPR) AND AUTOMATED EXTERNAL DEFIBRILLATOR (AED) APPARATUS AND METHOD

(76) Inventor: Sahar Anis Madanat, Zarka (JO)

( * ) Notice: Subject to any disclaimer, the term of this patent is extended or adjusted under 35 U.S.C. 154(b) by 644 days.

(21) Appl. No.: 13/564,851

(22) Filed: Aug. 2, 2012

(65) Prior Publication Data

US 2014/0039359 A1    Feb. 6, 2014

(51) Int. Cl.
*A61H 31/00* (2006.01)
*A61N 1/39* (2006.01)

(52) U.S. Cl.
CPC .......... *A61H 31/005* (2013.01); *A61H 31/007* (2013.01); *A61N 1/39* (2013.01); *A61H 2201/501* (2013.01); *A61H 2201/5043* (2013.01); *A61H 2230/06* (2013.01); *A61N 1/3993* (2013.01)

(58) Field of Classification Search
CPC ..... A61N 1/39; A61N 1/3993; A61H 31/004; A61H 31/005; A61H 31/007; A61H 31/008; A61H 2230/06; A61H 2201/501; A61H 2201/5043
USPC .............. 601/15, 41–44; 607/3, 5, 7; 128/898
See application file for complete search history.

(56) References Cited

U.S. PATENT DOCUMENTS

| 2004/0162510 | A1* | 8/2004 | Jayne et al. | 601/41 |
| 2007/0219588 | A1* | 9/2007 | Freeman | 607/5 |
| 2008/0177341 | A1* | 7/2008 | Bowers | 607/5 |
| 2008/0300518 | A1* | 12/2008 | Bowes | 601/41 |
| 2009/0024175 | A1* | 1/2009 | Freeman | 607/6 |
| 2011/0202100 | A1* | 8/2011 | Tan et al. | 607/5 |

* cited by examiner

*Primary Examiner* — Quang D Thanh
(74) *Attorney, Agent, or Firm* — Rahman LLC

(57) ABSTRACT

A combined cardio pulmonary resuscitation (CPR) and automated external defibrillator (AED) system for performing an emergency procedure over the clothing of a patient is provided. The system includes a spinal support rest having a cushion that accommodates a neck portion of the patient, a compression pad operatively connected to the spinal support rest and is adapted to be placed over the patient such that the compression pad is aligned above the heart and chest of the patient. A first arm strap and a second arm strap operatively connected to the compression pad. A power button automatically dials an emergency number to contact a medical professional. An interactive communication unit activates a two way real time video conference with the medical professional on the display to receive a set of instructions from the medical professional in real time to enable a user to perform the emergency procedure on the patient.

20 Claims, 9 Drawing Sheets

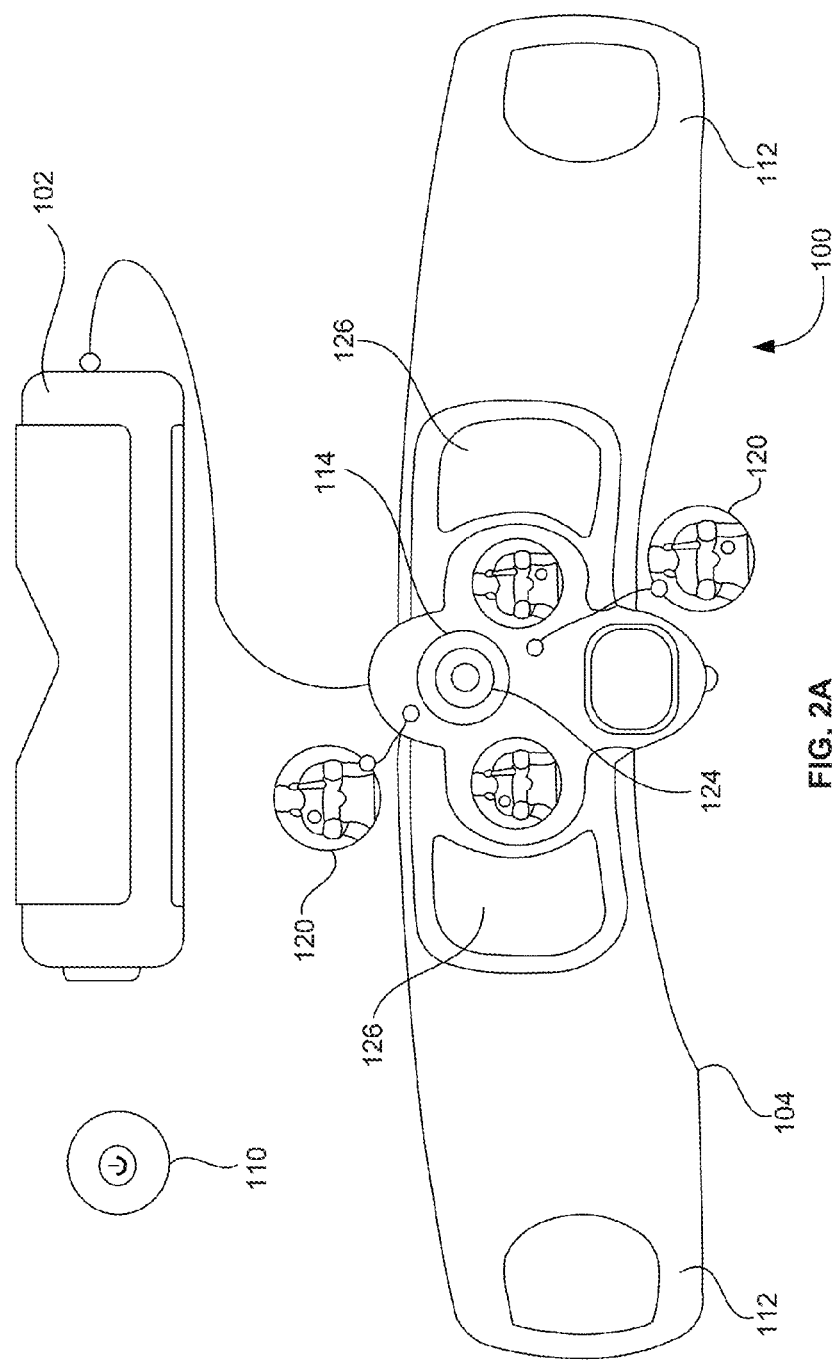

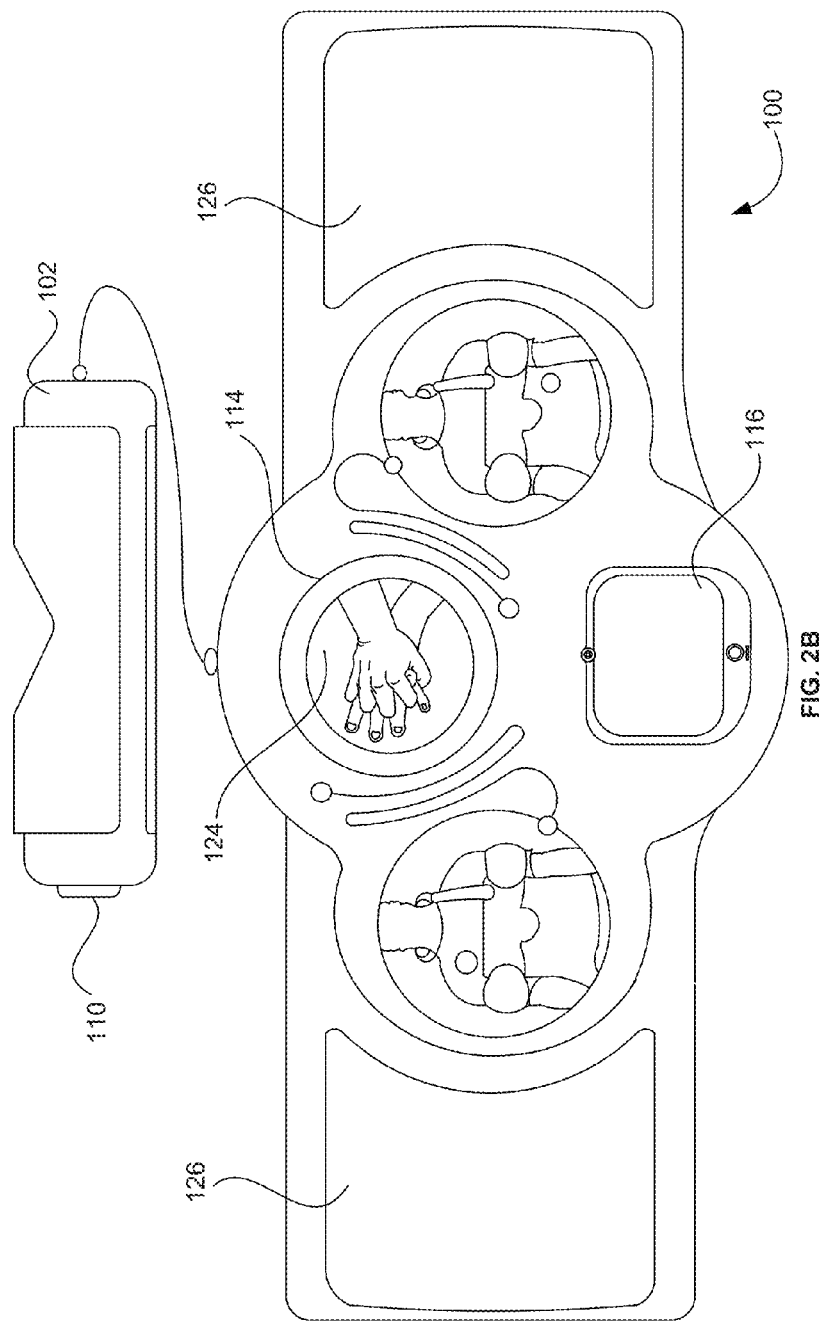

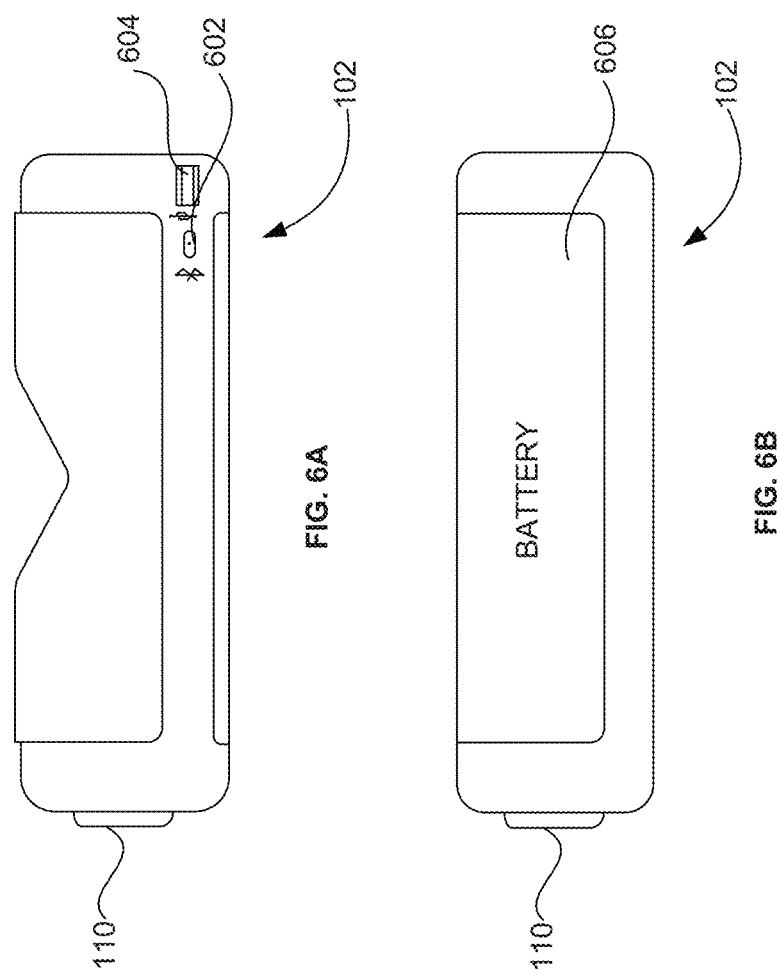

COMBINED CARDIO PULMONARY RESUSCITATION (CPR) AND AUTOMATED EXTERNAL DEFIBRILLATOR (AED) APPARATUS AND METHOD

BACKGROUND

1. Technical Field

The embodiments herein generally relate to medical kits for performing emergency procedures, and, more particularly, to a combined Cardio Pulmonary Resuscitation (CPR) and Automated External Defibrillator (AED) apparatus and a method for performing an emergency procedure to treat sudden cardiac arrest using the apparatus.

2. Description of the Related Art

Many lives are lost due to a Sudden Cardiac Arrest (SCA) every year. In fact, SCA is a leading cause of death in the United States. Such deaths can be prevented if effective emergency rescue procedures such as Cardio Pulmonary Resuscitation (CPR) and defibrillation are administered within 3-5 minutes of the onset of the SCA. To perform the emergency rescue procedures in such a short time, a skilled and trained person (e.g., a paramedic) is required. Typically, starting a CPR procedure in the case of a SCA, includes having an attending person, who is attending to the patient, run to a phone and dial an emergency number (e.g., 911). Then, the attending person must start administering the CPR procedure by positioning the patient on their back, tilting the head of the patient back and putting their chin up to keep his/her airway (e.g., a passageway by which air passes from the nose or mouth to the lungs) clear. The attending person should check for breathing or a pulse, and if none found, then the attending person gives two very strong breaths to the patient (mouth-to-mouth). Furthermore, the attending person must locate the position of the heart, and give thirty strong compressions downward (approximately 2 inches in depth) into the patient's chest. The sequences must be repeated until further help (e.g., emergency technician) arrives.

If an AED is available, the person attending to the victim, will have to also in addition to the above, have to remove all upper garments of the patient apply the electrode pads on the patients bare chest and follow the recorded voice instructions. An AED is a portable electronic device that automatically diagnoses potentially life-threatening cardiac arrhythmias of ventricular fibrillation and ventricular tachycardia in a patient. The AED is used to treat the patient through defibrillation, the application of electrical therapy which stops the arrhythmia, allowing the heart to reestablish an effective rhythm. Some AEDs may use an electronic voice to prompt users through each step. Because the user of an AED may be hearing impaired, AEDs may include visual prompts as well. However, a user who is inexperienced in performing the procedure may not be able to keep up with the pre-programmed or stored robotic electronic voice and understand the instructions clearly, particularly under a stressful situation such as administering emergency care to a person undergoing a SCA. For example when CPR is required, the conventional AED units only prompt the user to start CPR without further guidance.

Too many lives are lost to cardiac arrest every year, because the appropriate medical response was simply not available in time. There is a mere 5% current survival rate of SCAs, and less than 1% of SCA victims survive without permanent brain damage after suffering 4-6 minutes of a SCA. However, the average time for paramedics to arrive at the scene of the SCA is approximately 8 minutes, when chances of survival would have already dropped drastically. Research has indicated a 50-74% survival rate when CPR and AED are performed within 3-5 minutes of the SCA, where there is a mere 5% chance of survival when only CPR is performed; and a 20% chance of survival when only AED is performed. The chances of survival drop 10% every 60 seconds since the onset of SCA.

Moreover, approximately 84% of SCAs occur at home where there are no trained medical professionals. The risk of coronary heart disease increases with age, therefore the elderly are at highest risk. The elderly may be typically living alone or with only their spouse. Thus typically, when an SCA occurs, a family member or spouse may be the only one available in proximity of the patient. Current solutions require the family member, in the case of a SCA to a loved one at home, to run and call an emergency number, and then run to get a home defibrillator (if available), and then back to the patient. Then, they require the family member to take the victim's upper garments completely off before even starting the procedures to save the patient.

Furthermore, when CPR to the victim is needed, a conventional emergency machine may only prompt a user to start CPR, thus assuming that the user will remember all the steps, and have the stamina to give strong breaths and chest compressions as well as setting up the AED machine flawlessly. Finally, all this would have to be done within the first 5 minutes of the SCA. Therefore, the conventional solutions are not generally designed for an average person to use, let alone the elderly. Rather, the conventional solutions are typically designed for fast acting, young and recently CPR trained individuals. Furthermore, the conventional solutions generally only cater to either CPR or AED individually. Accordingly, there is a need for a combined CPR and AED apparatus that can be easily used in case of emergency by non-medical professionals within the first 3-5 minutes of the SCA.

SUMMARY

In view of the foregoing, an embodiment herein provides a combined cardio pulmonary resuscitation (CPR) and automated external defibrillator (AED) system for performing an emergency procedure comprising CPR and AED shock on a patient. The system includes a spinal support rest having a cushion that accommodates a neck portion of the patient, a compression pad operatively connected to the spinal support rest. The compression pad is adapted to be placed over the patient such that the compression pad is aligned above the heart and chest of the patient. The system includes a first arm strap and a second arm strap operatively connected to the compression pad, a power button that automatically dials an emergency number to contact a medical professional, and an interactive communication unit operatively connected to the compression pad. The interactive communication unit includes a display. The interactive communication unit activates a two way real time video conference with the medical professional on the display to receive a set of instructions from the medical professional in real time to enable a user to perform the emergency procedure on the patient.

The compression pad includes a first arm strap holder and a second arm strap holder. The first arm strap holder locks the first arm strap, and the second arm holder locks the second arm strap such that a first arm and a second arm of the patient are strapped adjacent to the patient. The system may further include a pair of electrode pads that are operatively connected to the compression pad, a heartbeat sensor that determines a heart rate of the patient. The heart rate is used to determine when a shock is to be administered to the patient. The first arm strap may include a first under arm pad. The second arm strap may include a second under arm pad. The first under arm pad accommodates a first under arm of the patient. The second under arm pad accommodates a second under arm of the patient. The pair of electrode pads are stuck by the user to a portion of clothing of the patient.

In another aspect, a cardio pulmonary resuscitation (CPR) and automated external defibrillator (AED) apparatus for performing an emergency procedure comprising CPR and AED shock on a patient is provided. The CPR and AED apparatus includes a spinal support having a cushion adapted to be placed under a neck of the patient, a compression pad that is operatively connected to the spinal support. The compression pad is adapted to be placed over the patient such that the compression pad is aligned above the heart and chest of the patient. A first arm strap and a second arm strap are operatively connected to the compression pad. The first arm strap includes a first under arm pad. The second arm strap includes a second under arm pad. The first under arm pad is adapted to accommodate a first under arm of the patient. The second under arm pad is adapted to accommodate a second under arm of the patient. A first arm strap holder and a second arm strap holder that respectively locks the first arm strap and the second arm strap such that a first arm and a second arm of the patient are strapped adjacent to the patient. A pair of sticky back electrode pads that may be operatively connected to the compression pad. The sticky back electrode pads are adapted to be adhered on clothing of the patient.

The apparatus may further include a power button that automatically dials an emergency number to contact a medical professional when the power button is turned on, an interactive communication unit that is operatively connected to the compression pad. The interactive communication unit includes a display. The interactive communication unit activates a two way real time video conference on the display with the medical professional. The interactive communication unit receives a set of instructions from the medical professional in real time to enable a user to perform the emergency procedure on the patient. The apparatus may further include a heartbeat sensor that is adapted to determine a pulse of the first under arm and the second under arm of the patient.

The compression pad is a semi-soft compression pad having a pair of sticky back electrode pad holders that are adapted to accommodate the pair of sticky back electrode pads. The compression pad exerts the user's force downwards and through an internal base and spreads the force along a sternum of the patient. The spinal support includes a neck curve spinal support that provides spinal support to the neck of the patient. The neck curve spinal support is a non-slip material.

The interactive communication unit enables the user to transfer data of the patient to the medical professional. The interactive communication unit includes a display, a high definition (HD) camera proximate to the display, a microphone proximate to the display, a plurality of speakers proximate to the display, and an emergency stop button that is adapted to terminate the emergency procedure and maintain the two way real time video conference.

In yet another aspect, a method of performing an emergency procedure comprising CPR and AED shock on a patient using a combined CPR and AED apparatus is provided. The method includes providing support to a neck portion of the patient using a spinal support rest, placing a compression pad over the patient, strapping a first arm and a second arm of the patient using a first arm strap and a second arm strap, respectively, configuring an interactive communication unit having a display, activating and displaying a two way real time video conference on the display, and performing the emergency procedure based on a set of instructions received from a medical professional and video tutorials displayed on the display. The interactive communication unit is adapted to receive the set of instructions from the medical professional in real time to enable a user to perform the emergency procedure on the patient when the CPR and AED apparatus is powered on.

The method may further include automatically dialing an emergency number to connect with the medical professional when the CPR and AED apparatus is turned on. A heart rate of the patient may be determined using a heartbeat sensor that is operatively connected to the compression pad. The first arm and the second arm of the patient may be strapped adjacent to the patient. A pulse of the first under arm and the second under arm of the patient using the heartbeat sensors may be determined to perform the emergency procedure over clothing of the patient.

The first arm and the second arm are secured away from the user when a shock is to be administered to the patient based on the pulse of the first under arm and the second under arm of the patient. A force may be exerted downwards onto the compression pad by the user and through an internal base and spreading the force along a sternum of the patient using the compression pad.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2A illustrates a front view of the CPR and AED kit of FIG. 1A according to an embodiment herein;

FIG. 2B illustrates a front view of the CPR and AED kit of FIG. 1A illustrating a layout of wires connected between the compression pad and the pair of electrode pads of FIG. 1A according to an embodiment herein;

FIG. 6A illustrates a rear view of the head rest unit of the CPR and AED kit of the FIG. 1A according to an embodiment herein;

FIG. 6B illustrates a bottom view of the head rest unit of the CPR and AED kit of the FIG. 1A according to the embodiments herein;

DETAILED DESCRIPTION OF PREFERRED EMBODIMENTS

Figure 1A:
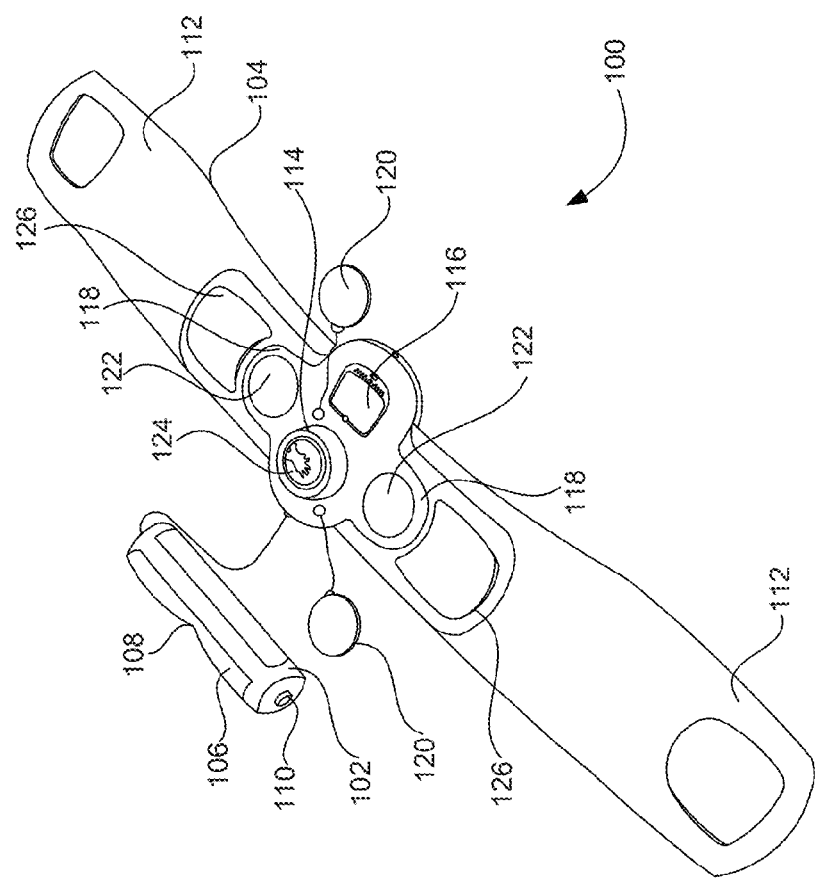
FIG. 1A illustrates a perspective view of a Cardio Pulmonary Resuscitation (CPR) and Automated External Defibrillator (AED) kit for performing an emergency procedure on a patient during the onset of Sudden Cardiac Arrest (SCA) according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there is a need for a combined CPR and AED apparatus that can be easily used in case of emergency by non-medical professionals to perform an emergency procedure during the onset of a SCA. The embodiments herein achieve this by providing a combined CPR and AED kit which is capable being used without having to remove the patient's upper garments, and that establishes an interactive video conference with an Emergency Medical Technician (EMT) to receive instructions in real time to operate the portable CPR and AED kit. Referring now to the drawings, and more particularly to FIGS. 1A through 8, where similar reference characters denote corresponding features consistently throughout the figures, preferred embodiments are described herein.

FIG. 1A illustrates a perspective view of a Cardio Pulmonary Resuscitation (CPR) and Automated External Defibrillator (AED) kit 100 for performing an emergency procedure on a patient during the onset of Sudden Cardiac Arrest (SCA) according to an embodiment herein. The CPR and AED kit 100 includes a head rest unit 102 and a flexible blanket unit 104. The head rest unit 102 may include a spinal support rest 106 with an ergonomic neck curve 108 and a power button 110 among other features as further described below. The flexible blanket unit 104 includes a pair of arm straps 112, a compression pad 114, and an interactive communication unit 116. The scale of the illustrations of the CPR and AED kit 100 may be skewed for presentational purposes, in one example embodiment. In one embodiment, the spinal support rest 106 comprises an ergonomic neck curve spinal support that includes a cushion that is adapted to accommodate a neck portion of a patient.

The spinal support rest 106 is placed under the neck portion of the patient. The spinal support rest 106 helps to open the patient's airway and facilitates a continuous oxygen supply to brain cells of the patient especially during compressions. The compression pad 114 is operatively connected to the spinal support rest 106. In one embodiment, the power button 110 automatically dials an emergency number (e.g., 911) to contact a medical professional (e.g., a medical expert, an Emergency Medical Technician, or a paramedic, etc.) when the power button 110 is turned ON. In one embodiment, the power button 911 includes 4G wireless phone capabilities or WiFi or other wireless protocols, and includes GPS location capabilities.

The compression pad 114 may be placed over the patient and automatically aligned above the heart and the chest of the patient for an optimal cardio pulmonary resuscitation (CPR) and an optimal automated external defibrillation (AED) technique. In one embodiment, the compression pad 114 comprises a semi-soft anti slip compression pad. The semi-soft anti slip compression pad 114, when used, exerts the operator's force downwards to the vertebrae and along the entire sternum of the patient to reduce the possibility of breaking of the ribs in the patient. The pair of arms straps 112 is operatively connected to the semi-soft anti slip compression pad for strapping arms of the patient. The compression pad 114 includes an ergonomic curved groove 124 configured for focused effort, which is especially helpful for the elderly.

The interactive communication unit 116 includes a display. The interactive communication unit is operatively connected to the compression pad 114. The interactive communication unit 116 activates a two way real time video conference on the display with the medical professional. The interactive communication unit 116 receives a set of instructions from the medical professional in real time to enable a user to perform the emergency procedure on the patient. The compression pad 114 includes a pair of arm strap holders 118. The arm strap holders 118 lock the pair of arm straps 112 such that the arms are strapped closely to the patient and away from the operator, in the case that an electric shock is given to the patient. The arm straps 112 may be made of water proof fabric and expandable material.

The CPR and AED kit 100 includes a pair of electrode pads 120 that are operatively connected to the compression pad 114. The pair of electrode pads 120 may comprise stick back electrode pads that can be used to stick to a portion of clothing of the patient and may include graphics that clearly show their location on the patient. The CPR and AED kit 100 further includes a pair of sticky back electrode pad holders 122 that accommodate the pair of electrode pads 120. The spinal support rest 106 may be made of an injection molded plastic material, in one example embodiment. The ergonomic neck curve 108 is made of a semi soft injection molded silicon or rubber which exhibits anti-slip property, in one example embodiment.

The CPR and AED kit 100 includes a heartbeat sensor (which are configured in the under arm pads 126) that determines a heartbeat rate of the patient. The heartbeat sensor may determine a heart rate of the patient to determine the level of shock to be administered to the patient. The shock is given through the electrode pads 120; one at the top and the other at the bottom corner and cross the heart of the patient. The embodiments herein allow for the shock to be administered over the clothing of the patient and not under the clothing thereby saving valuable rescue/resuscitation time. The pair of arm straps 112 includes a pair of under arm pads 126 (e.g., a first under arm pad, and a second under arm pad) that accommodate a first under arm and a second under arm of the patient. This enables the ability to secure the arms of the patient (e.g., a first arm and a second arm) against the patient's body and away from the user when the shock is administered based on a pulse of the first under arm and the second under arm of the patient.

Figure 1B:
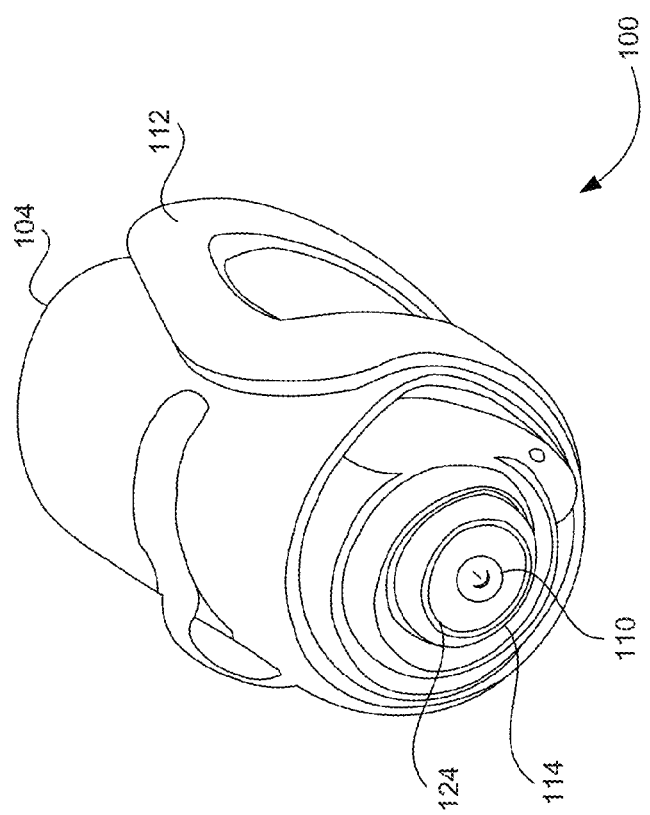
FIG. 1B is a perspective view illustrating a compact configuration of the CPR and AED kit of FIG. 1A according to an embodiment herein.

With reference to FIG. 1A, FIG. 1B is a perspective view illustrating a compact configuration of the CPR and AED kit 100 of FIG. 1A according to an embodiment herein. As shown in FIG. 1B, the entire CPR and AED kit 100 may roll into a compact configuration to provide ease of storage and mobility.

With reference to FIG. 1A, FIG. 2A illustrates a front view of the CPR and AED kit 100 of FIG. 1A according to the embodiments herein. With reference to FIG. 1A through FIG. 2A, FIG. 2B illustrates a front view of the CPR and AED kit 100 of FIG. 1A illustrating a layout of wires operatively connected between the compression pad 114 and the pair of electrode pads 120 of FIG. 1A according to an embodiment herein.

Figure 3:
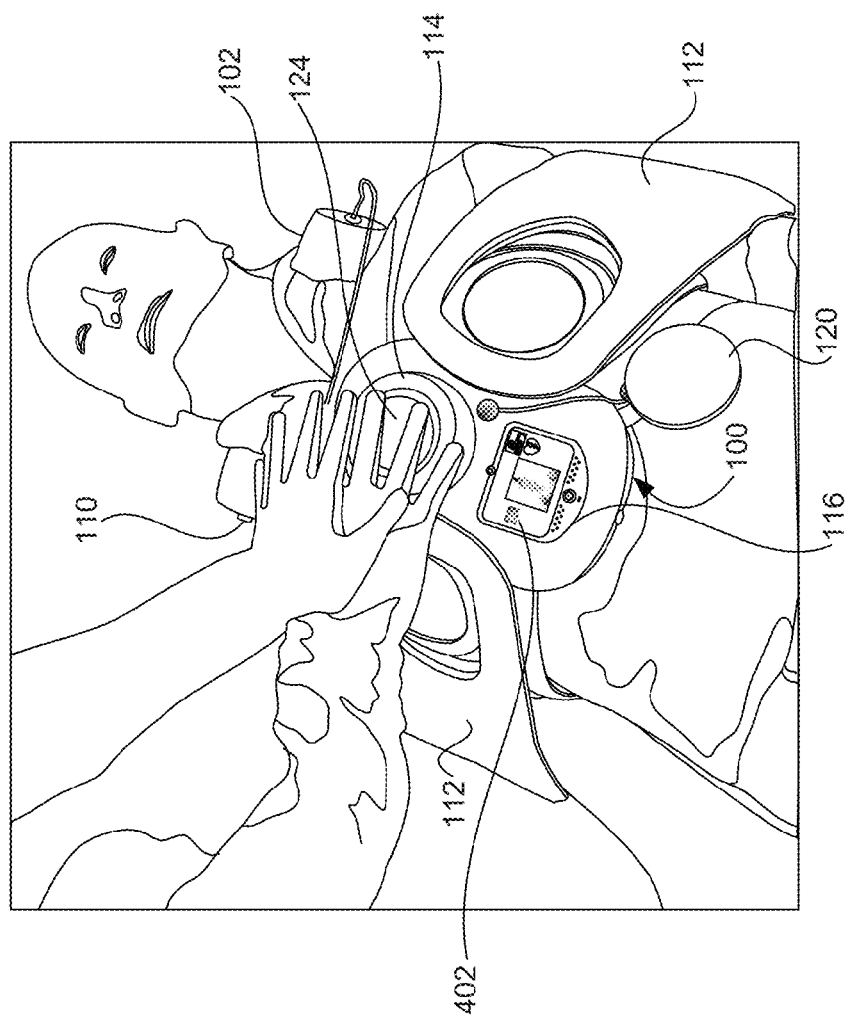
FIG. 3 is an exemplary view illustrating a method of using the CPR and AED kit of FIG. 1A to perform the emergency procedure on a patient according to an embodiment herein.

FIG. 3, with reference to FIGS. 1A through 2B, is an exemplary view illustrating a method of using the CPR and AED kit 100 of FIG. 1A to perform an emergency procedure on the patient according to the embodiments herein. The head rest unit 102 is positioned under the neck portion of the patient. The compression pad 114 of the flexible blanket unit is positioned over the chest of the patient. The arm straps 112 are strapped and locked in the arm strap holder 118 such that the arms are close to the patient as shown in FIG. 3.

An untrained user can receive instructions in real time from a medical professional and perform CPR and AED treatment with the help of a video conference on a display 402 of the interactive communication unit 116. The display 402 shows a set of instructions to operate the CPR and AED kit 100 and to perform the emergency procedure. In one embodiment, the emergency procedure is performed over clothing of the patient. The set of instructions may include one or more video tutorials on how to operate the CPR and AED kit 100 and to perform the CPR and AED treatments correctly. A force may be exerted by the user or medical professional or an assistant by pressing the compression pad 114 as shown in FIG. 3.

Figure 4:
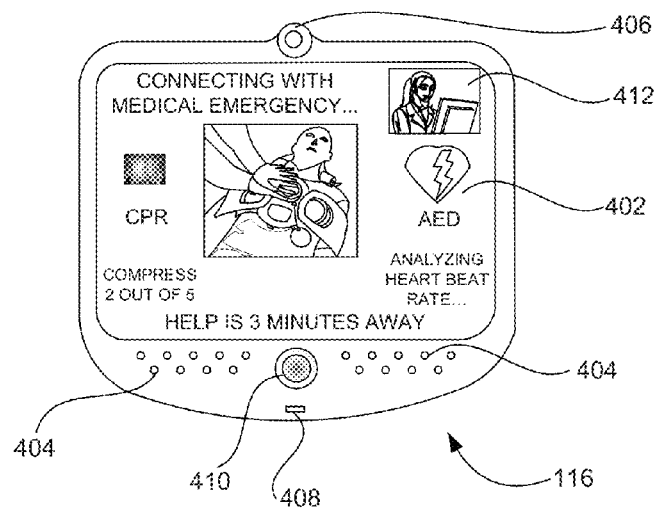
FIG. 4 illustrates the interactive communication unit of the CPR and AED kit of FIG. 1A according to an embodiment herein.

FIG. 4, with reference to FIGS. 1A through 3, illustrates the interactive communication unit 116 of the CPR and AED kit 100 of FIG. 1A according to an embodiment herein. The interactive communication unit 116 includes a display 402, one or more speakers 404, a video camera 406, a microphone 408, and an emergency stop button 410. The display 402 displays one or more tutorials to perform the emergency procedure. The display 402 further provides one or more updates (e.g., compress 2 out of 5, etc.), and displays a heart rate analysis of the patient (e.g., when the electrode pads are stuck to the patient, etc.). In one embodiment, the display 402 comprises a high definition (HD) screen of sufficient size to permit ease of viewing by the user (e.g., approximately 7.9 cm, in one example embodiment).

The video camera 406 allows an assistant to interact with the medical professional on a real time basis (e.g., a live video call interface 412) to guide the assistant/the user or the patient through every step of performing the CPR and AED treatments. In one embodiment, the video camera 406 comprises a HD camera. The microphone 408 is operatively connected to the HD camera 406. The one or more speakers 404 are operatively connected to the HD camera 406 and the microphone 408. The one or more speakers 404 and the microphone 408 enable the patient, or the assistant/user to listen and speak to the medical professional or the paramedic via the live video call. The HD camera 406, the microphone 408, and the one or more speakers 404 are in proximate to the display 402.

The emergency stop button 410 allows stopping the operation of the CPR and AED kit 100. The emergency stop button 410 may be used to terminate the emergency procedure and maintain the two way real time video conference. The interactive communication unit 116 may be configured to be wirelessly linked and wireless capable, include a universal serial bus (USB) port(s) 604 (shown in FIG. 6A), and Bluetooth™ communication ready, thus enabling the user to transfer life saving data of the patient to the medical professional after each use. The interactive communication unit 116 activates a two way real time video conference with medical professional (e.g., a medical technician or a paramedic) on the display 402. The medical professional provides a set of instructions in real time to operate the CPR and AED kit 100 and to perform the emergency procedure.

Figures 5A, 5B:
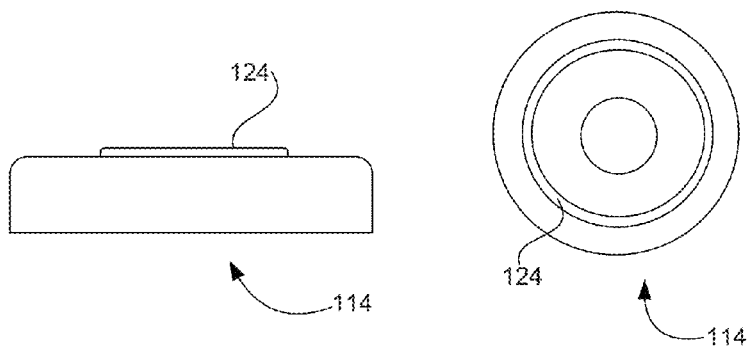
FIG. 5A illustrates a side view of the protruding compression pad of the CPR and AED kit of FIG. 1A according to an embodiment herein.
FIG. 5B illustrates a top view of the compression pad of the CPR and AED kit of FIG. 1A according to an embodiment herein.

With reference to FIG. 1A, FIG. 5A illustrates a side view of the compression pad 114 of the CPR and AED kit 100 of FIG. 1A according to the embodiment herein. With reference to FIG. 1A, FIG. 5B illustrates a top view of the compression pad 114 of the CPR and AED kit 100 of FIG. 1A according to the embodiment herein. The compression pad 114 includes the groove 124 for providing a focused force downward to the heart of the patient through an internal base of the compression pad 114. The internal base of the compression pad 114 spreads the force along the entire sternum of the patient, which reduces the chance of breaking the patient's ribs while administering the emergency procedures.

With reference to FIGS. 1A through 5B, FIG. 6A illustrates a rear view of the head rest unit 102 of the CPR and AED kit 100 of the FIG. 1A according to an embodiment herein. With reference to FIGS. 1A through 6A, FIG. 6B illustrates a bottom view of the head rest unit 102 of the CPR and AED kit 100 of the FIG. 1A according to an embodiment herein. The rear view of the head rest unit 102 illustrates a Bluetooth™ communication button 602, and an USB port 604. The bottom view of the head rest unit 102 illustrates a battery source 606 to provide power for the CPR and AED kit 100. The Bluetooth™ communication button 602 and the USB port 604 allows for the quick transfer of life-saving data/information to the medical professional.

Figure 7:
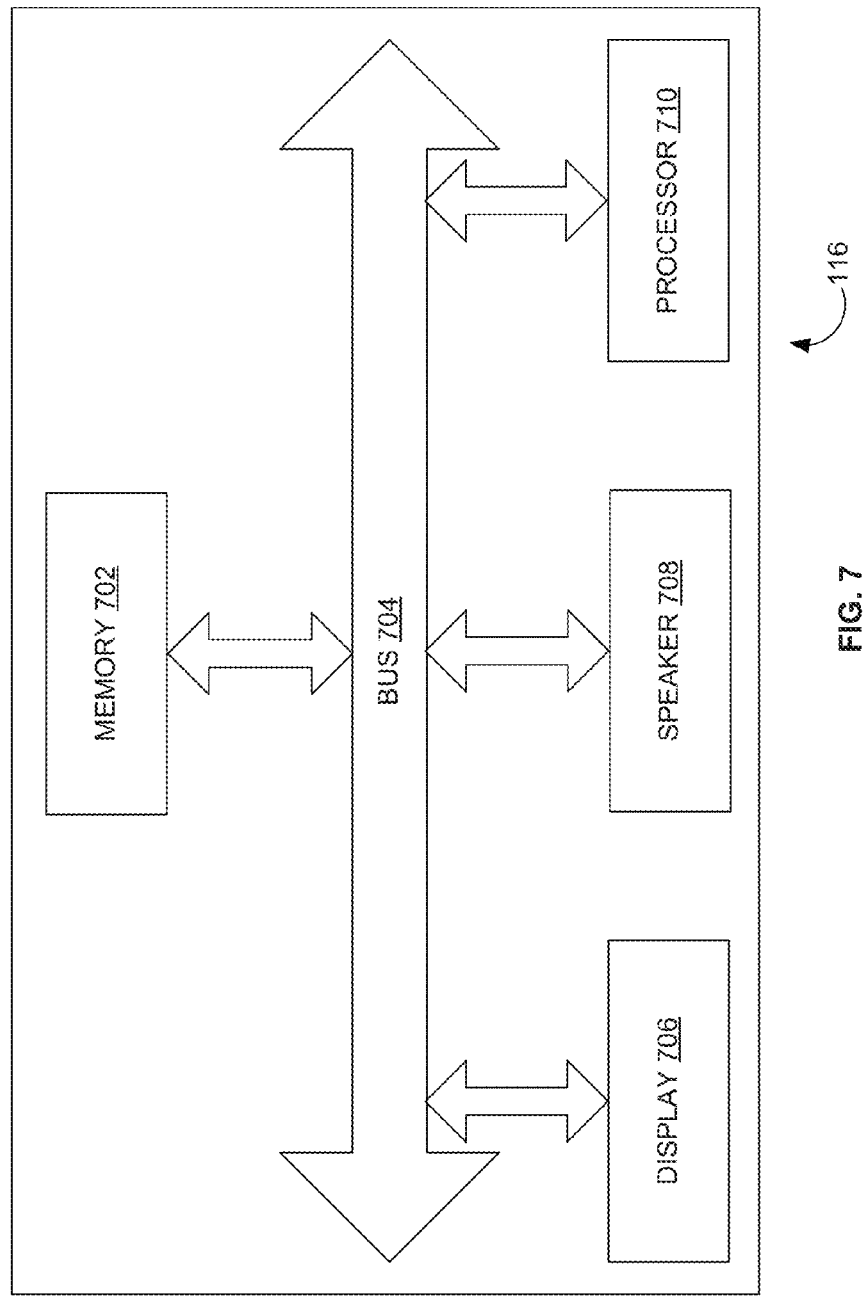
FIG. 7 illustrates a schematic diagram of the interactive communication unit of FIG. 1A used in accordance with the embodiments herein.

FIG. 7, with reference to FIGS. 1A through 6B, illustrates a schematic diagram of the interactive communication unit 116 of FIG. 1A having an a memory 702 having a set of computer instructions, a bus 704, a display 706, a speaker 708, and a processor 710 capable of processing a set of computer instructions to perform any one or more of the methodologies herein, according to an embodiment herein. The processor 710 may also enable digital content to be consumed in the form of video for output via one or more displays 706 or audio for output via speaker and/or earphones 508. The processor 710 may also carry out the methods described herein and in accordance with the embodiments herein.

Digital content may also be stored in the memory 702 for future processing or consumption. The memory 702 may also store program specific information and/or service information (PSI/SI), including information about digital content (e.g., the detected information bits) available in the future or stored from the past. A user of the interactive communication unit 116 may view this stored information on display 706 (e.g., the display 402 of FIG. 4) and select an item of for viewing, listening, or other uses via input, which may take the form of keypad, scroll, or other input device(s) or combinations thereof. When digital content is selected, the processor 710 may pass information. The content and PSI/SI may be passed among functions within the interactive communication unit 116 of FIG. 1A of the user using the bus 704.

Figure 8:
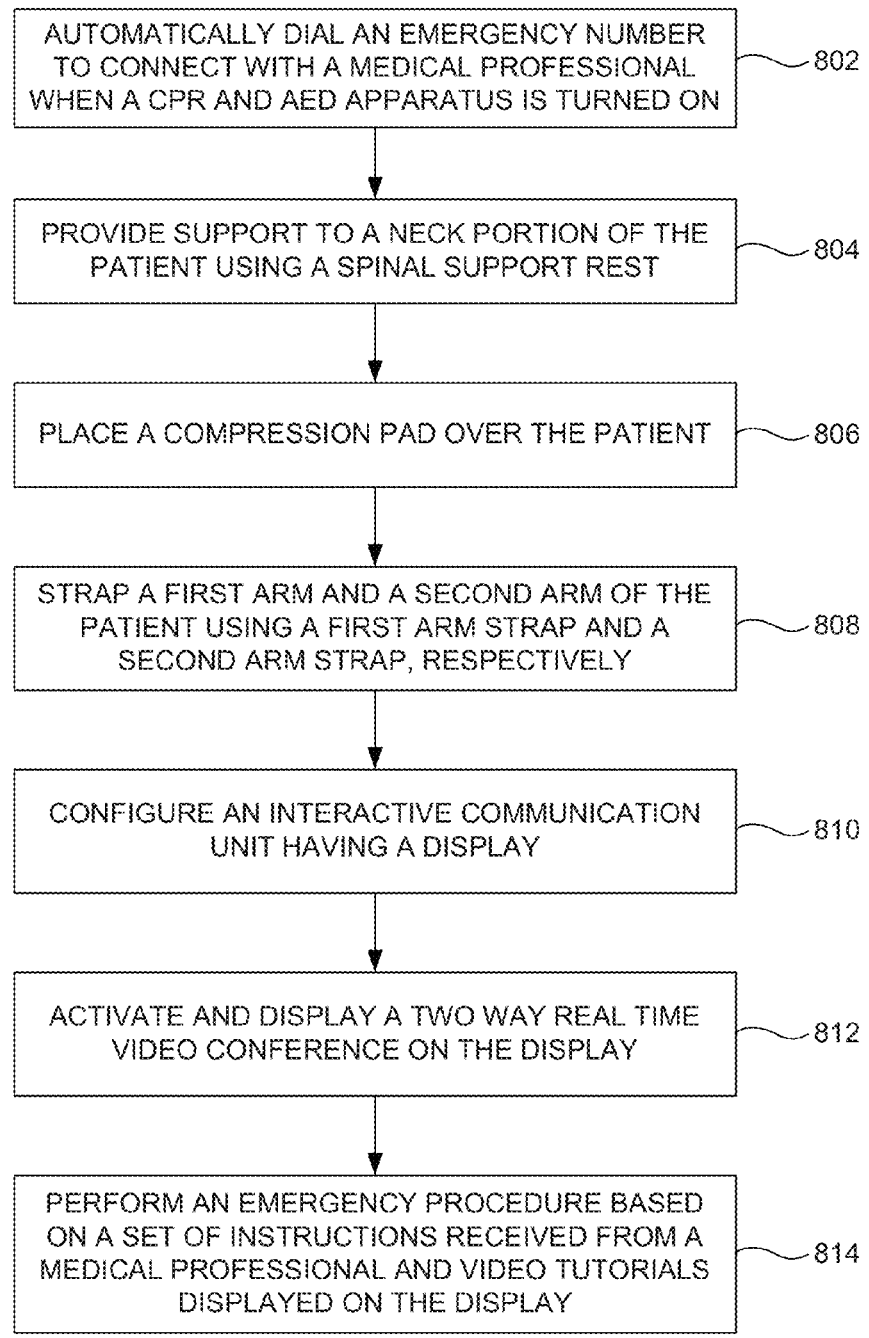
FIG. 8 is a flow diagram illustrating a method according to an embodiment herein.

FIG. 8, with reference to FIG. 1A through 7, is a flow diagram illustrating a method of performing an emergency procedure on a patient to treat a cardiac arrest using the CPR and AED kit 100 according to an embodiment herein. In step 802, an emergency number is automatically dialed to connect with a medical professional when the CPR and AED kit 100 is turned on. In step 804, support to a neck portion of the patient is provided using the spinal support rest 106. In step 806, the compression pad 114 is placed over the patient. In step 808, a first arm and a second arm of the patient are strapped using a first arm strap and a second arm strap, respectively (e.g., the pair of arm straps 112). In step 810, the interactive communication unit 116 having the display 402 is configured. In step 812, a two way real time video conference is activated and displayed on the display 402. The interactive communication unit 116 is adapted to receive a set of instructions from a medical professional in real time to enable a user to perform the emergency procedure on the patient when the CPR and AED kit 100 is powered on. In step 814, the emergency procedure is performed based on the set of instructions received from the medical professional and video tutorials displayed on the display 402.

A heart rate of the patient may be determined using a heartbeat sensor (not shown) that is operatively connected to the compression pad 114. The first arm and the second arm of the patient are strapped adjacent to the patient. A pulse of the first under arm and the second under arm of the patient may be determined to perform the emergency procedure over clothing of the patient. The first arm and the second arm are secured away from the user when a shock is to be administered to the patient based on the pulse of the first under arm and the second under arm of the patient. A force may be exerted downwards and through an internal base and the force is spread along a sternum of the patient using the compression pad 114.

The CPR and AED kit 100 allows for the performance of an emergency procedure (e.g., CPR and defibrillation) over the clothing of a patient. The CPR and AED kit 100 includes the head rest unit 102, and the flexible blanket unit 104, which may be waterproof, operatively connected to the head rest unit 102. This arrangement opens the patient's airway, thereby allowing oxygen to continuously serve the brain cells of the patient. This reduces the chances of brain damage (e.g., reduces the chance of damage to brain cells) in the patient. The CPR and AED kit 100 automatically dials an emergency number (e.g., 911) to contact a medical professional for attending a medical emergency on the patient when the power button 110 is turned ON. Additionally, the CPR and AED kit 100 initiates the heartbeat sensor (not shown) to determine whether a shock is to be provided to the patient and what level the shock is to be administered. The CPR and AED kit 100 includes the interactive communication unit 116 that activates a two way real time video conference with medical professional (e.g., a paramedic or a medical technician) on the display 402.

The interactive communication unit 116 receives a set of instructions from the medical professional in real time (e.g., through the two way real time video conference) to enable a user to perform the emergency procedure on the patient. The set of instructions guides the patient or the assistant/operator/user (e.g., person who is attending to the patient) through every step of the CPR/AED procedure. This increases the chances of patient survival by 50-74%. Additionally, the arm straps 112 secure the arms of the patient away from the operator/assistant when a shock is administered. The CPR and AED kit 100 allows the user to perform both CPR and AED treatments on the patient by allowing an assistant to follow the AED and CPR audio and visual tutorials displayed in the display 402 of the interactive communication unit 116. The semi-soft anti slip compression pad 114, which is automatically positioned over the patient's heart and optimizes compressions, focuses force downward and through an internal base, spreading the force along the vertebrae of the patient which reduces the chances of breaking ribs in the patient.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A combined cardio pulmonary resuscitation (CPR) and automated external defibrillator (AED) system for performing an emergency procedure comprising CPR and AED shock on a patient, said system comprising:
    a spinal support rest comprising a cushion that accommodates a neck portion of said patient;
    a compression pad operatively connected to said spinal support rest, wherein said compression pad is adapted to be placed over said patient such that said compression pad is aligned above the heart and chest of said patient;
    a first arm strap and a second arm strap operatively connected to said compression pad;
    a power button that automatically dials an emergency number to contact a medical professional; and
    an interactive communication unit operatively connected to said compression pad, wherein said interactive communication unit comprises a display, wherein said interactive communication unit activates a two way real time video conference with said medical professional on said display to receive a set of instructions from said medical professional in real time to enable a user to perform said emergency procedure on said patient.

2. The system of claim 1, wherein said compression pad comprises a first arm strap holder and a second arm strap holder, wherein said first arm strap holder locks said first arm strap, and said second arm holder locks said second arm strap such that a first arm and a second arm of said patient are strapped adjacent to said patient.

3. The system of claim 1, further comprising a pair of electrode pads operatively connected to said compression pad.

4. The system of claim 1, further comprising a heartbeat sensor that determines a heart rate of said patient, wherein said heart rate is used to determine when a shock is to be administered to said patient.

5. The system of claim 4, wherein said first arm strap comprises a first under arm pad, wherein said second arm strap comprises a second under arm pad, wherein said first under arm pad accommodates a first under arm of said patient, and wherein said second under arm pad accommodates a second under arm of said patient.

6. The system of claim 3, wherein said pair of electrode pads are stuck to a portion of clothing of said patient.

7. A cardio pulmonary resuscitation (CPR) and automated external defibrillator (AED) apparatus for performing an emergency procedure comprising CPR and AED shock on a patient, said CPR and AED apparatus comprising:
    a spinal support comprising a cushion adapted to be placed under a neck of said patient;
    a compression pad operatively connected to said spinal support, wherein said compression pad is adapted to be placed over said patient such that said compression pad is aligned above the heart and chest of said patient;

a first arm strap and a second arm strap operatively connected to said compression pad, wherein said first arm strap comprises a first under arm pad, wherein said second arm strap comprises a second under arm pad, wherein said first under arm pad is adapted to accommodate a first under arm of said patient, and wherein said second under arm pad is adapted to accommodate a second under arm of said patient;

a first arm strap holder and a second arm strap holder that respectively locks said first arm strap and said second arm strap such that a first arm and a second arm of said patient are strapped adjacent to said patient; and a pair of sticky back electrode pads operatively connected to said compression pad, wherein said sticky back electrode pads are adapted to be adhered on clothing of said patient.

8. The apparatus of claim 7, further comprising a power button that automatically dials an emergency number to contact a medical professional when said power button is turned on.

9. The apparatus of claim 7, further comprising an interactive communication unit that is operatively connected to said compression pad, wherein said interactive communication unit comprises a display, wherein said interactive communication unit activates a two way real time video conference on said display with said medical professional, wherein said interactive communication unit receives a set of instructions from said medical professional in real time to enable a user to perform said emergency procedure on said patient.

10. The apparatus of claim 7, further comprising a heartbeat sensor that is adapted to determine a pulse of said first under arm and said second under arm of said patient.

11. The apparatus of claim 8, wherein said compression pad comprises a semi-soft compression pad comprising a pair of sticky back electrode pad holders that are adapted to accommodate said pair of sticky back electrode pads, wherein said compression pad exerts a force downwards and through an internal base and spreads said force along a sternum of said patient.

12. The apparatus of claim 7, wherein said spinal support comprises a neck curve spinal support that provides spinal support to said neck of said patient, wherein said neck curve spinal support comprises non-slip material.

13. The apparatus of claim 9, wherein said interactive communication unit enables said user to transfer data of said patient to said medical professional, and wherein said interactive communication unit comprises:

a high definition (HD) camera proximate to said display;

a microphone proximate to said display;

a plurality of speakers proximate to said display; and an emergency stop button that is adapted to terminate said emergency procedure and maintain said two way real time video conference.

14. A method of performing an emergency procedure comprising of cardio pulmonary resuscitation (CPR) and automated external defibrillator (AED) shock on a patient using a combined CPR and AED apparatus, said method comprising:

providing support to a neck portion of said patient using a spinal support rest;

placing a compression pad over said patient;

strapping a first arm and a second arm of said patient using a first arm strap and a second arm strap, respectively;

configuring an interactive communication unit having a display;

activating and displaying a two way real time video conference on said display, wherein said interactive communication unit is adapted to receive a set of instructions from a medical professional in real time to enable a user to perform said emergency procedure on said patient when said CPR and AED apparatus is powered on; and performing said emergency procedure based on said set of instructions received from said medical professional and video tutorials displayed on said display.

15. The method of claim 14, further comprising automatically dialing an emergency number to connect with said medical professional when said CPR and AED apparatus is turned on.

16. The method of claim 14, further comprising determining a heart rate of said patient using a heartbeat sensor that is operatively connected to said compression pad.

17. The method of claim 16, further comprising strapping said first arm and said second arm of said patient adjacent to said patient.

18. The method of claim 17, further comprising determining a pulse of a first under arm and a second under arm of said patient using heartbeat sensors to perform said emergency procedure over clothing of said patient.

19. The method of claim 18, further comprising securing said first arm and said second arm away from said user when a shock is to be administered to said patient based on said pulse of said first under arm and said second under arm of said patient.

20. The method of claim 14, further comprising exerting a force downwards and through an internal base and spreading said force along a sternum of said patient using said compression pad.

\* \* \* \* \*